(12) United States Patent
Condie et al.

(10) Patent No.: US 9,532,828 B2
(45) Date of Patent: Jan. 3, 2017

(54) SYSTEM AND METHOD FOR ADAPTIVE RF ABLATION

(75) Inventors: Catherine R. Condie, Shoreview, MN (US); Marshall L. Sherman, Cardiff by the Sea, CA (US); Kathryn E. Kasischke, San Diego, CA (US); Timothy J. Corvi, Carlsbad, CA (US); Aaron R. Strunk, San Diego, CA (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 905 days.

(21) Appl. No.: 13/096,236

(22) Filed: Apr. 28, 2011

(65) Prior Publication Data

US 2012/0136348 A1 May 31, 2012

Related U.S. Application Data

(60) Provisional application No. 61/417,629, filed on Nov. 29, 2010.

(51) Int. Cl.
*A61B 18/18* (2006.01)
*A61B 18/14* (2006.01)
(Continued)

(52) U.S. Cl.
CPC .......... *A61B 18/14* (2013.01); *A61B 18/1206* (2013.01); *A61B 18/1492* (2013.01);
(Continued)

(58) Field of Classification Search
CPC ............ A61B 18/1206; A61B 18/1233; A61B 2018/0016; A61B 2018/00214; A61B 2018/00351; A61B 2018/00577; A61B 2018/00636; A61B 2018/00642; A61B 2018/00648;A61B 2018/00696; A61B 2018/00702; A61B 2018/00726; A61B 2018/00732; A61B 2018/00714; A61B 2018/00791; A61N 1/3682
(Continued)

(56) References Cited

U.S. PATENT DOCUMENTS 3,461,261 A * 8/1969 Lewis et al. .................. 219/693
4,074,719 A * 2/1978 Semm .............................. 606/31
(Continued)

FOREIGN PATENT DOCUMENTS

CN    101563040 A    10/2009
CN    101720213 B     6/2013

OTHER PUBLICATIONS

Eick et al., "The LETR-Principle: A Novel Method to Assess Electrode-Tissue Contact in Radiofrequency Ablation", Journal of Cardiovascular Electrophysiology, vol. 9, No. 11, Nov. 1998, pp. 1180-1185.
(Continued)

*Primary Examiner* — Michael Peffley
*Assistant Examiner* — Yasamin Ekrami
(74) *Attorney, Agent, or Firm* — Greg A. McAllister

(57) ABSTRACT

A medical method, device, and system are provided, including advancing an ablation element of a medical device into contact with tissue to be treated, selecting a power level of energy to ablate the tissue, delivering energy at the selected power level to the ablation element, determining whether the ablation element is in continuous contact with the tissue, and reducing the selected power level when the ablation element ceases to be in continuous contact with the tissue.

12 Claims, 15 Drawing Sheets

(51) Int. Cl.
*A61B 18/12* (2006.01)
*A61B 18/00* (2006.01)

(52) U.S. Cl.
CPC .......... *A61B 2018/0016* (2013.01); *A61B 2018/00214* (2013.01); *A61B 2018/00267* (2013.01); *A61B 2018/00351* (2013.01); *A61B 2018/00577* (2013.01); *A61B 2018/00642* (2013.01); *A61B 2018/00648* (2013.01); *A61B 2018/00678* (2013.01); *A61B 2018/00702* (2013.01); *A61B 2018/00714* (2013.01); *A61B 2018/00726* (2013.01); *A61B 2018/00779* (2013.01); *A61B 2018/00791* (2013.01); *A61B 2090/065* (2016.02)

(58) Field of Classification Search
USPC ............. 606/20, 22, 23, 33, 39, 40, 41, 45
See application file for complete search history.

(56) References Cited

U.S. PATENT DOCUMENTS

| | | | |
|---|---|---|---|
| 4,446,874 A * | 5/1984 | Vaguine | 607/156 |
| 4,637,346 A * | 1/1987 | Draper et al. | 122/4 A |
| 4,685,459 A * | 8/1987 | Koch et al. | 606/51 |
| 4,840,177 A * | 6/1989 | Charbonnier | A61N 1/3937 600/547 |
| 5,596,995 A | 1/1997 | Sherman et al. | |
| 5,713,933 A * | 2/1998 | Condie et al. | 607/28 |
| 5,810,802 A * | 9/1998 | Panescu et al. | 606/31 |
| 5,869,971 A * | 2/1999 | Sherman | 324/439 |
| 5,971,980 A | 10/1999 | Sherman | |
| 6,050,994 A | 4/2000 | Sherman | |
| 6,059,778 A | 5/2000 | Sherman | |
| 6,123,702 A * | 9/2000 | Swanson et al. | 606/34 |
| 6,179,833 B1 * | 1/2001 | Taylor | 606/34 |
| 6,200,314 B1 | 3/2001 | Sherman | |
| 6,312,452 B1 * | 11/2001 | Dobak et al. | 607/105 |
| 6,391,024 B1 | 5/2002 | Sun et al. | |
| 6,488,678 B2 | 12/2002 | Sherman | |
| 6,494,880 B1 * | 12/2002 | Swanson | A61B 18/1206 606/34 |
| 6,558,378 B2 | 5/2003 | Sherman et al. | |
| 6,752,804 B2 | 6/2004 | Simpson et al. | |
| 6,761,716 B2 | 7/2004 | Kadhiresan et al. | |
| 6,936,024 B1 * | 8/2005 | Houser | 604/22 |
| 7,270,656 B2 * | 9/2007 | Gowda et al. | 606/15 |
| 8,586,897 B2 * | 11/2013 | Cronin | 219/690 |
| 2002/0123749 A1 * | 9/2002 | Jain | 606/41 |
| 2003/0045908 A1 * | 3/2003 | Condie et al. | 607/9 |
| 2006/0106375 A1 | 5/2006 | Werneth et al. | |
| 2006/0142752 A1 | 6/2006 | Ormsby et al. | |
| 2006/0259024 A1 * | 11/2006 | Turovskiy et al. | 606/33 |
| 2006/0264923 A1 * | 11/2006 | Prakash et al. | 606/33 |
| 2007/0016180 A1 * | 1/2007 | Lee et al. | 606/33 |
| 2007/0083193 A1 | 4/2007 | Werneth et al. | |
| 2007/0260242 A1 * | 11/2007 | Dycus et al. | 606/51 |
| 2008/0269851 A1 * | 10/2008 | Deem et al. | 607/101 |
| 2008/0300588 A1 * | 12/2008 | Groth et al. | 606/34 |
| 2009/0076336 A1 * | 3/2009 | Mazar et al. | 600/300 |
| 2009/0076409 A1 * | 3/2009 | Wu et al. | 600/547 |
| 2009/0131926 A1 * | 5/2009 | Rusin et al. | 606/33 |
| 2009/0234351 A1 * | 9/2009 | Desinger et al. | 606/35 |
| 2010/0004528 A1 | 1/2010 | Weiss et al. | |
| 2010/0168738 A1 | 7/2010 | Schneider et al. | |
| 2010/0286687 A1 * | 11/2010 | Feldberg et al. | 606/33 |

OTHER PUBLICATIONS 21819B-319PW (PCT/US2011/060610) PCT Notification of Transmittal of the International Search Report and the Written Opinion of the International Searching Authority, Mailed May 3, 2012, 14 pages.
The State Intellectual Property Office of the People's Republic of China, Notice on the First Office Action and Search Report for Application/Patent No. 201180057169.5, Dec. 1, 2014, 12 pages.

* cited by examiner

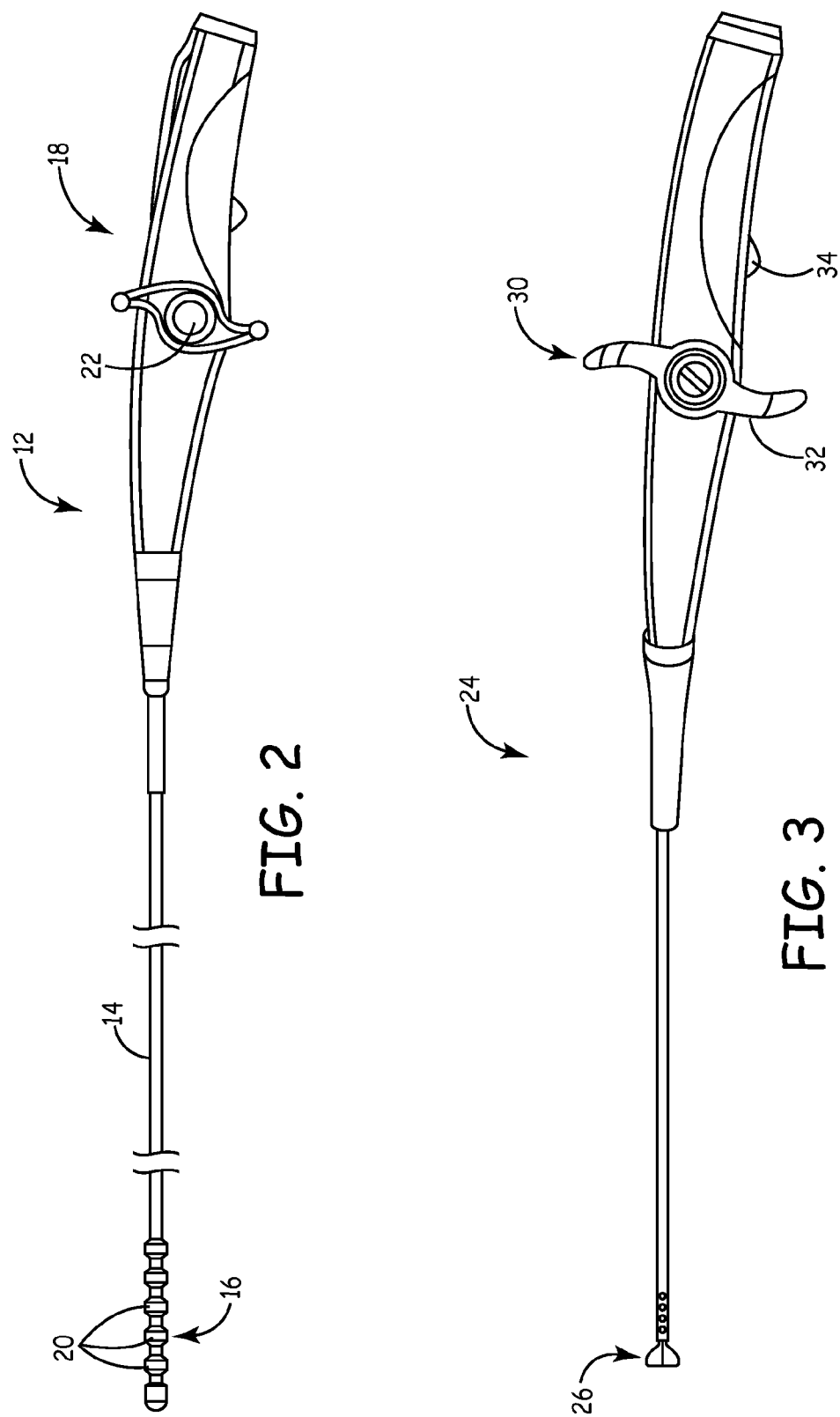

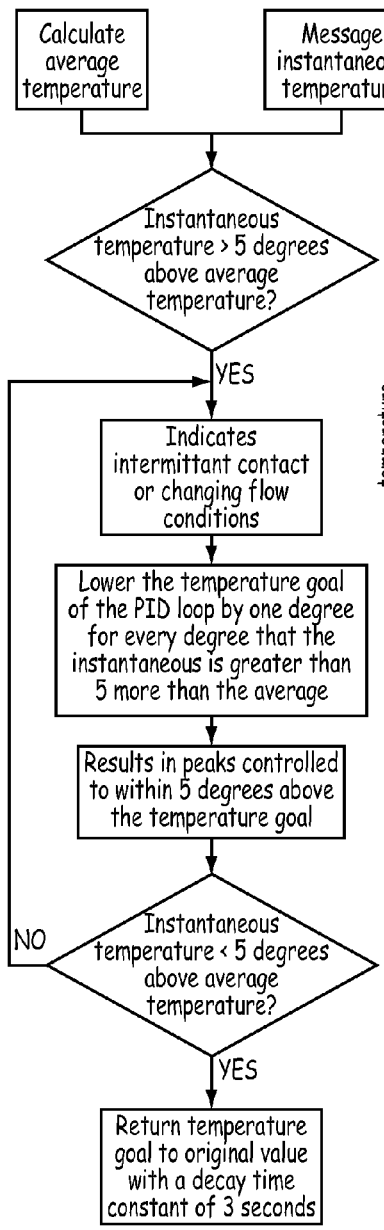
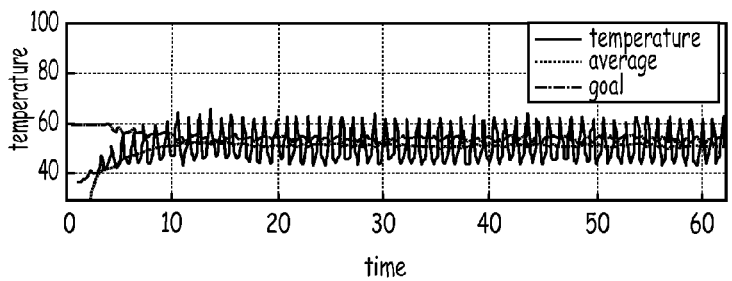
FIG. 11
FIG. 10

SYSTEM AND METHOD FOR ADAPTIVE RF ABLATION

CROSS-REFERENCE TO RELATED APPLICATIONS

This application claims the benefit of U.S. Provisional Application No. 61/417,629 filed on Nov. 29, 2010.

Cross-reference is hereby made to the commonly-assigned related U.S. application Ser. No. 13/096,255, entitled "System and Method for Adaptive RF Ablation" filed concurrently herewith and incorporated herein by reference in it's entirety.

STATEMENT REGARDING FEDERALLY SPONSORED RESEARCH OR DEVELOPMENT

N/A

FIELD OF THE INVENTION

The present invention relates to medical systems and methods for ablation of tissue, including cardiac tissue.

BACKGROUND

Medical procedures are used to treat a variety of cardiovascular defects, such as cardiac arrhythmias, atrial fibrillation, and other irregularities in the transmission of electrical impulses through the heart. Such medical procedures may involve ablation of the specific tissue that cause or transmit the irregular electrical impulses, e.g., creating lesions or other anatomical effects that disrupt or block electrical pathways through the targeted tissue so as to allow the other tissues to function properly. In the treatment of cardiac arrhythmias for example, a specific area of cardiac tissue having aberrant electrical activity (e.g. focal trigger, slow conduction, excessively rapid repolarization, fractionated electrogram, etc.) may be identified first and then treated.

One example of a type of ablation system involves the delivery of radiofrequency ("RF") energy to the tissue selected for treatment. RF ablation systems may include a power source or RF generator, and one or more medical devices having at least one ablation element or electrode coupled to the power source. The medical device may be a flexible catheter having a handle at a proximal end and an ablation electrode near a distal end, or may have an array of electrodes which may be configured on one or more carrier arms. Examples of an RF generator and medical ablation catheters having various configurations are illustrated in FIGS. 1-7. One or more sensors may also be provided, such as a temperature sensor, thermocouple, or a sensor for another parameter (such as contact assessment, pressure, etc.), which may be arranged at or near the ablation electrodes. The sensors may be placed near to one or more of the ablating surface of each electrode, or at the interface between the electrode and the tissue to be treated. Such a system may also include one or more external electrodes touching the skin of the patient, which may be called "indifferent" electrodes, also coupled to the power source. After mapping and diagnosing the electrical irregularities, a physician may decide to treat the patient by ablating cardiac tissue. FIG. 8 shows a stylized depiction of an ablation system in use during a medical treatment of the heart of a patient.

It is desirable to enable and ensure continuous contact during an ablation procedure between each ablation element or electrode and the corresponding selected tissue. It is also desirable to maintain a constant electrode temperature during the ablation, at a value sufficiently high to ensure that lesions are created, but not so high that there is a risk of charring and coagulum formation. Feedback controllers that are responsive to a temperature measured at or near the electrodes may be employed to maintain electrode temperature. Sometimes the tissue selected for treatment may be moving, such as for example cardiac tissue of a beating heart, or during the movements associated with respiration.

During such movement, one or more ablation elements may lose contact or be in only intermittent contact with the tissue. When tissue contact is lost, the temperature of the ablation element will ordinarily decrease. In response, it is possible that a feedback controller of an ablation system may temporarily increase power output from the power source. Such a response may be an undesirable reaction to the temperature feedback signal, since the decreased temperature is caused by the loss of firm and continuous tissue contact, and not due to a change in the ablation conditions that would require additional power supplied to the ablation elements.

To provide more effective, safe and efficient medical treatments, it is desirable to optimize the ablation system and method of use to avoid excessive local heat which may cause the formation of coagulum. It is also desirable to monitor and recognize the level and character of contact by an ablation element with the corresponding tissue to be treated, and respond accordingly.

SUMMARY OF THE INVENTION

The present invention advantageously provides a medical device, system, and method for treating a patient by delivering energy to ablate tissue. The energy may be reduced during periods when an ablation element is not in contact, or has intermittent contact, with the tissue. In particular, a medical method is provided, including advancing an ablation element of a medical device into contact with tissue to be treated, selecting a power level of energy to ablate the tissue, delivering energy at the selected power level to the ablation element, determining whether the ablation element is in continuous contact with the tissue, and reducing or maintaining the selected power level when the ablation element ceases to be in continuous contact with the tissue. In a particular example, power may be provided to one or more ablation elements or electrodes until the electrode reaches a target temperature. The subsequent power delivery is then limited to the power delivery characteristics (e.g., such as duty cycle) that resulted in reaching the target temperature. In other words, the delivered power characteristics that resulted in the attained target temperature are set as a threshold for subsequent power delivery during the treatment. If the temperature of the electrode later drops below the previously-attained target temperature under the same or substantially similar power delivery conditions, an alert may be generated indicating that the electrode has lost sufficient contact with the target tissue.

A medical system is also provided, including a medical device having an ablation electrode, and a source of RF energy coupled to the ablation element, the source having a duty cycle, and having a variable power output, wherein the source of RF energy has a duty cycle with a base period between approximately 5 ms and approximately 20 ms.

A medical system is also provided, including a medical device having an ablation electrode and a temperature sensor, a source of RF energy in electrical communication with the ablation element, the source having a variable power output with a duty cycle of selectable duration within a base frequency, and a proportional-integral-derivative controller coupled to the temperature sensor and the source of RF energy, wherein the integral portion of the controller has a period at least equal to the duration of a heartbeat.

A medical method is also provided, including advancing an electrode of a medical device into contact with tissue to be treated, monitoring a temperature of the electrode, selecting a desired temperature and a threshold variation, delivering energy to the electrode, calculating an average temperature of the electrode, calculating a difference between the temperature and the average temperature, calculating a continuity value by subtracting the difference from the desired temperature, and reducing the desired temperature when the continuity value exceeds the threshold variation.

A medical method is also provided, including advancing an electrode of a medical device into contact with tissue to be treated, monitoring a temperature of the electrode, selecting a desired temperature and a threshold value, delivering energy at a duty cycle value associated with the temperature threshold to the electrode, setting a duty cycle limit equal to an initial duty cycle value, limiting the energy to a maximum of the duty cycle limit when the temperature value exceeds the threshold.

A medical method is also provided, including advancing an electrode of a medical device into contact with tissue to be treated, selecting a desired maximum power, delivering energy from a power source at a duty cycle value to the electrode, monitoring power produced by the power source, calculating average power produced by the power source, limiting the average power to the desired maximum power, setting a maximum duty cycle equal to the current duty cycle value when the power is at least equal to the desired maximum power, and thereafter limiting the duty cycle value to the maximum duty cycle.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIG. 2 is an illustration of an exemplary medical device constructed in accordance with the principles of the present invention;

FIG. 3 is an illustration of another exemplary medical device constructed in accordance with the principles of the present invention;

FIG. 10 is another flow chart of a medical method of use of the medical systems of FIGS. 1-8 in accordance with the principles of the present invention;

FIG. 11 is a graph illustrating exemplary parameters during the medical method of FIG. 10;

DETAILED DESCRIPTION OF THE INVENTION

Figure 1:
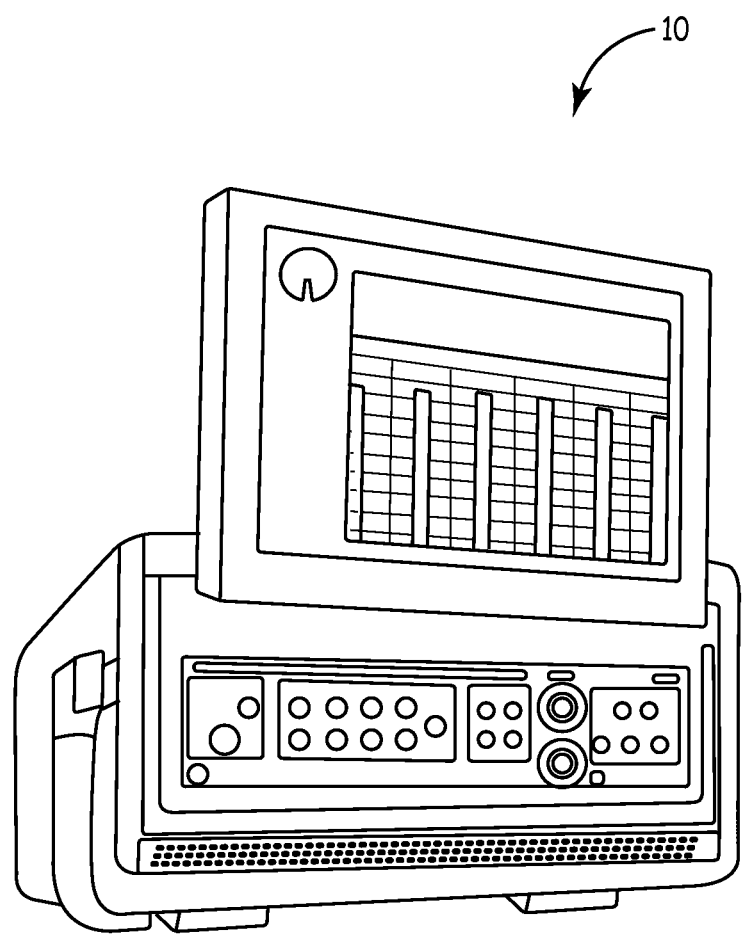
FIG. 1 is an illustration of an exemplary medical radiofrequency signal generator constructed in accordance with the principles of the present invention.

The present invention provides medical devices, systems and methods of use thereof for treating a patient, which may include ablating one or more selected tissue regions and providing a feedback or monitoring mechanism for determining whether an ablation device or element is in continuous contact with the selected tissue, and modifying the operation of the device accordingly. Referring now to the drawings in which like reference designators refer to like elements, there is shown in FIG. 1 an exemplary embodiment of a power source such as for example an RF generator constructed in accordance with the principles of the present invention, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

As shown in FIG. 1, the power source 10 may generally include a display or monitor, a console, operating controls, and couplings for connection to one or more medical devices, one or more patient return or "indifferent" electrodes, an ECG, a power cable, and/or other operating equipment. The power source 10 may have electronic circuitry to produce the desired ablation energy, to deliver it to the ablation elements of a medical device, to obtain feedback information or parameters from other sensors, and to operate, adjust, modulate or cease providing the ablation energy during a medical treatment of a patient, as well as to display or otherwise inform the physician.

Generally, the power source 10 may be operated in various modes which may be selected by the physician. For example, ablation energy may be supplied to one or more ablation elements in a bipolar mode, a unipolar mode, or a combination bipolar and unipolar mode. A unipolar mode of operation involves delivering energy between one or more ablation elements on a medical device and one or more patient return elements touching the skin of the patient. A bipolar mode of operation involves delivering energy between at least two ablation elements on a medical device. And a combination mode of operation involves delivering energy in both bipolar and unipolar modes simultaneously and/or intermittently. When in a combination mode of operation, it may be possible to select various ratios of activity or ablation energy among the bipolar and unipolar modes, including for example ratios such as 1:1, 2:1, or 4:1 (bipolar:unipolar).

The medical devices coupled to the power source 10 may be catheters or surgical probes, including for example an electrophysiology catheter having diagnostic and/or treatment components positionable at or near a target tissue region. For example, the medical device 12 illustrated in FIG. 2 may have a shape and dimensions to reach various treatments sites, such as intraluminal access to vascular anatomy, including for example transseptal access to the left atrium of a patient's heart for subsequent treatment or ablation. The medical device 12 may generally define an elongated, flexible catheter body 14 having a distal treatment assembly 16, as well as a handle assembly 18 at or near a proximal end of the catheter body. The distal treatment assembly 16 may, for example, include one or more ablation elements such as electrodes 20, each of which may be electrically coupled to the power source 10. The distal treatment assembly 16 of the medical device 12 has a linear shape, with a plurality of ablation elements or electrodes 20. The shaft may be both flexible and resilient, with sufficient column strength facilitating steady contact with tissue. This improves signal fidelity in diagnosing contacted tissue as well as improve therapeutic thermal exchange between the device and contacted tissue. The proximal handle assembly 18 has a rotational actuator 22 for manipulating, bending, steering and/or reshaping the distal treatment assembly into various desired shapes, curves, etc.

Figure 4:
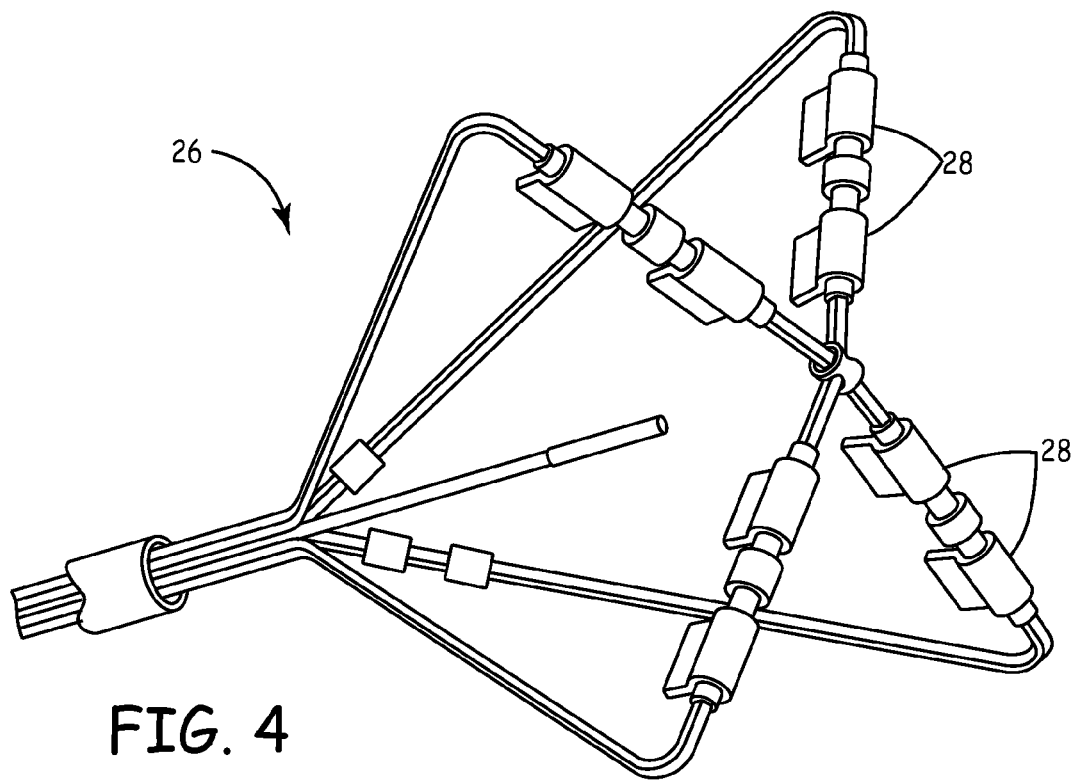
FIG. 4 is an illustration of a portion of the medical device of FIG. 3.
Figure 5:
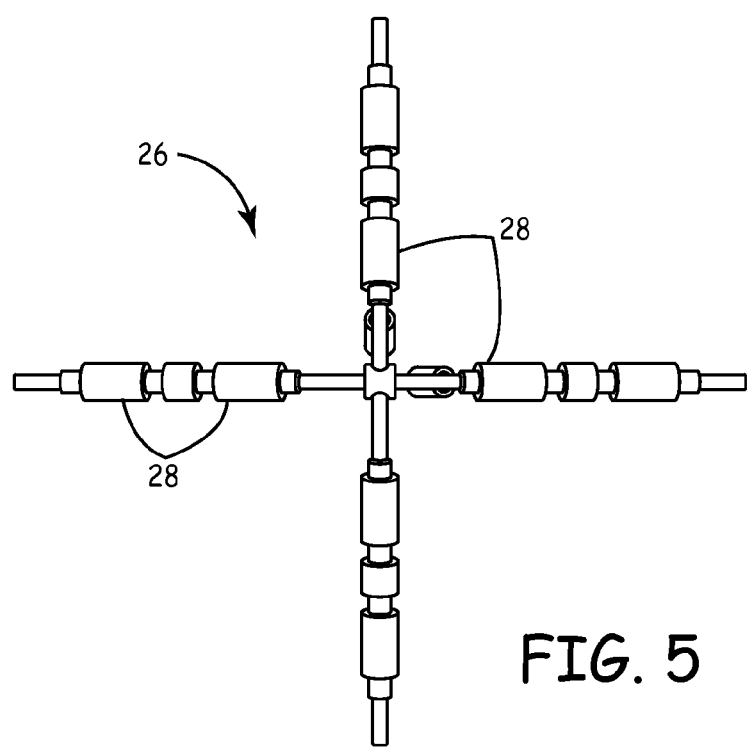
FIG. 5 is an illustration of a portion of the medical device of FIG. 3.

FIGS. 3-5 show a medical device or ablation catheter 24 with a catheter shaft and a distal treatment assembly 26 with compound carrier arms which may be resilient, so that in a deployed configuration the electrodes 28 have a generally planar arrangement. Similar to the medical device of FIG. 2, the distal treatment assembly 26 may be used for bipolar ablation, monopolar ablation, or a combination thereof. A proximal handle 30 has a rotational actuator 32 for manipulating a distal portion of the ablation catheter, and a linear actuator 34. The linear actuator 32 can advance the distal treatment assembly 26 distally beyond the catheter shaft, and retract the distal treatment assembly 26 proximally inside the catheter shaft. When the distal treatment assembly 26 is advanced distally, it may resiliently expand from a compressed arrangement inside the catheter shaft to the deployed arrangement shown in FIGS. 4 and 5.

Figure 6:
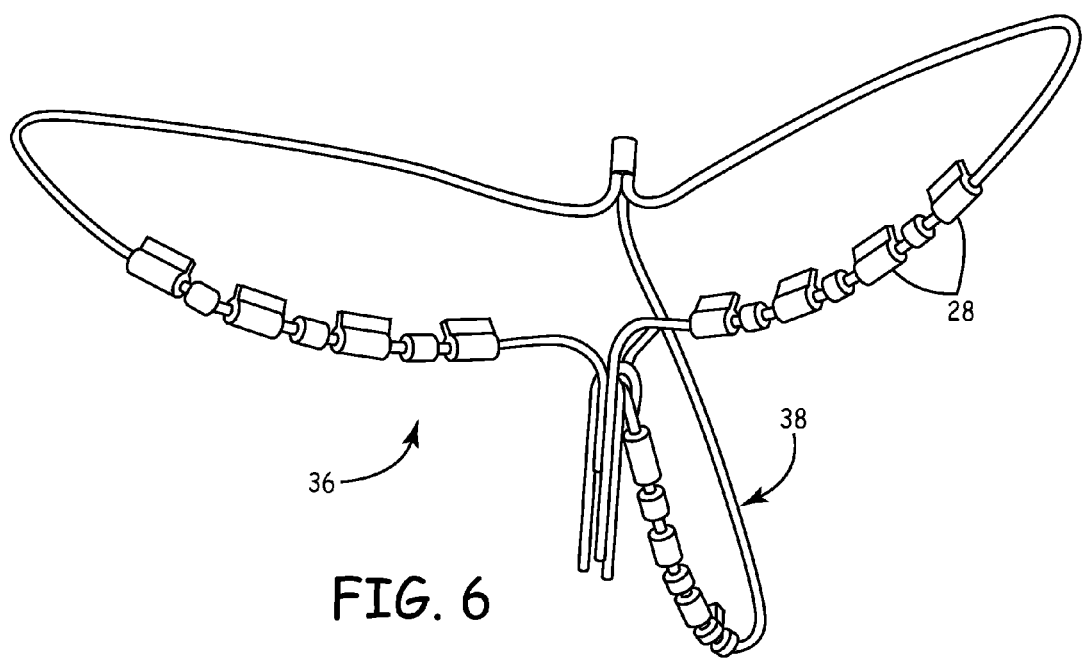
FIG. 6 is an illustration of another exemplary medical device constructed in accordance with the principles of the present invention.
Figure 7:
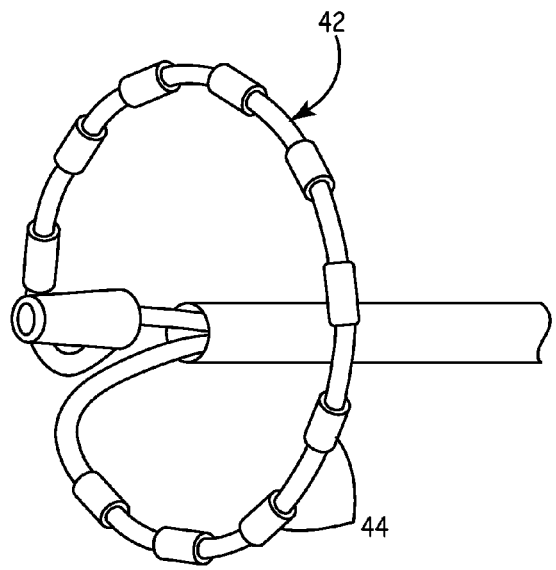
FIG. 7 is an illustration of yet another exemplary medical device constructed in accordance with the principles of the present invention.

A distal treatment assembly portion of a medical device or catheter 36 shown in FIG. 6 has a resilient framework of carrier arms 38, in which the electrodes 40 have a proximally-directed configuration, which may for example be used for transseptal treatments of a patient's heart. Another distal treatment assembly portion of a medical device or catheter 42 is depicted in FIG. 7, which has a distal treatment assembly having a deployed configuration in which the electrodes 44 have an adjustable linear, planar, or spiral configuration.

Figure 8:
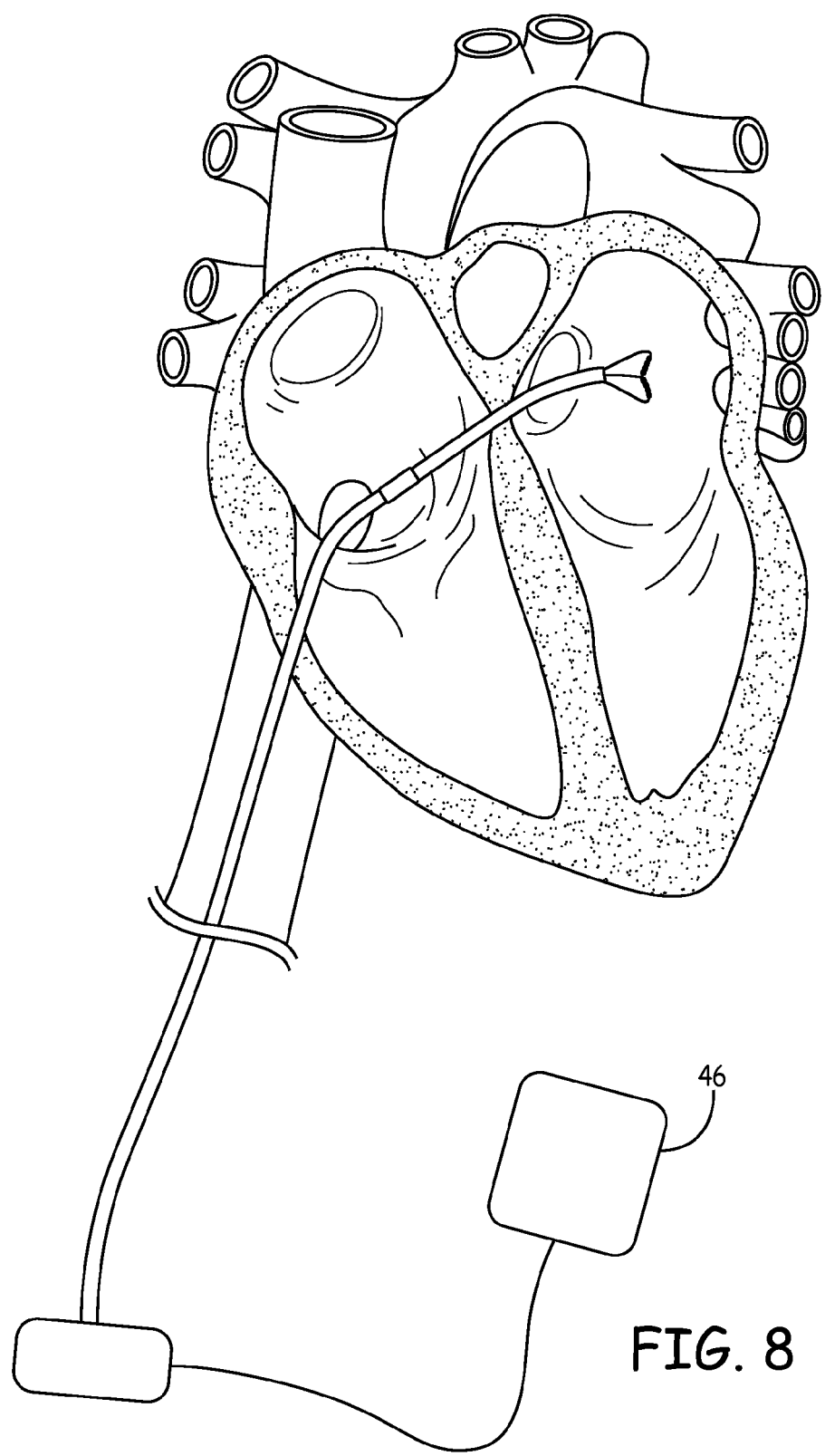
FIG. 8 is an illustration of an exemplary medical device during a medical procedure.

An indifferent or patient return electrode 46 may also be provided, as shown in FIG. 8 during an exemplary treatment of a patient's heart. The patient return electrode 46 may include a conductive pad having a greater surface area than the electrodes. The patient return electrode may be external to the patient, for example in contact with the patient's skin through an adhesive attachment to the back of the patient, and may be operably coupled to an ECG interface unit and/or directly to the power source or RF generator.

Accordingly, medical systems and devices may be used to investigate and treat aberrant electrical impulses or signals in a selected tissue region, such as for example in the cardiac tissues of a patient's heart. A distal treatment assembly of a medical device may be advanced through the patient's vasculature via the femoral artery or other access route and along a previously inserted guidewire. The distal treatment assembly may then be advanced, for example, into the right atrium and into proximity of a pulmonary vein.

Figure 9:
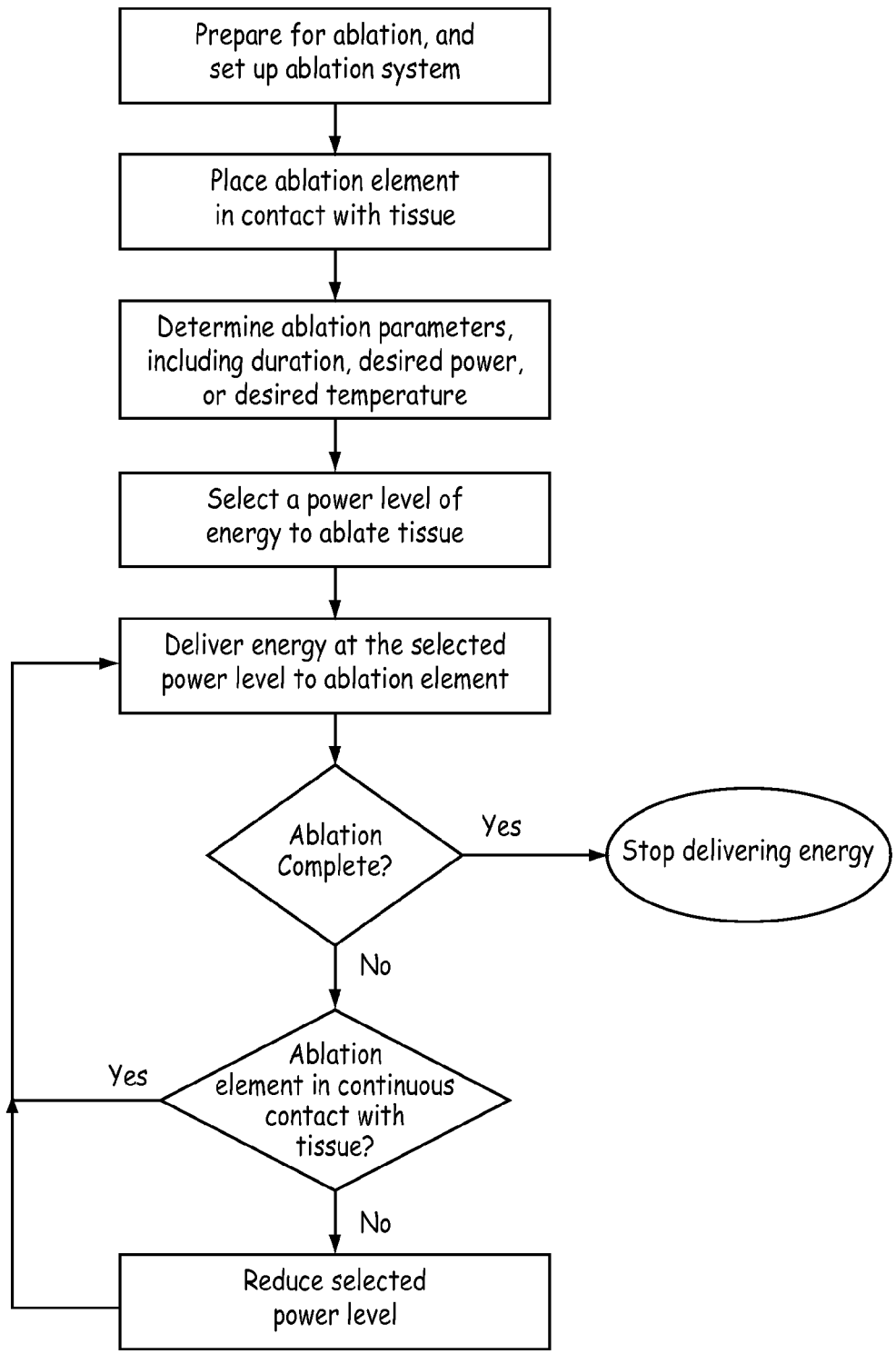
FIG. 9 is a flow chart of a medical method of use of the medical devices of FIGS. 1-8 in accordance with the principles of the present invention.
Figure 9A:
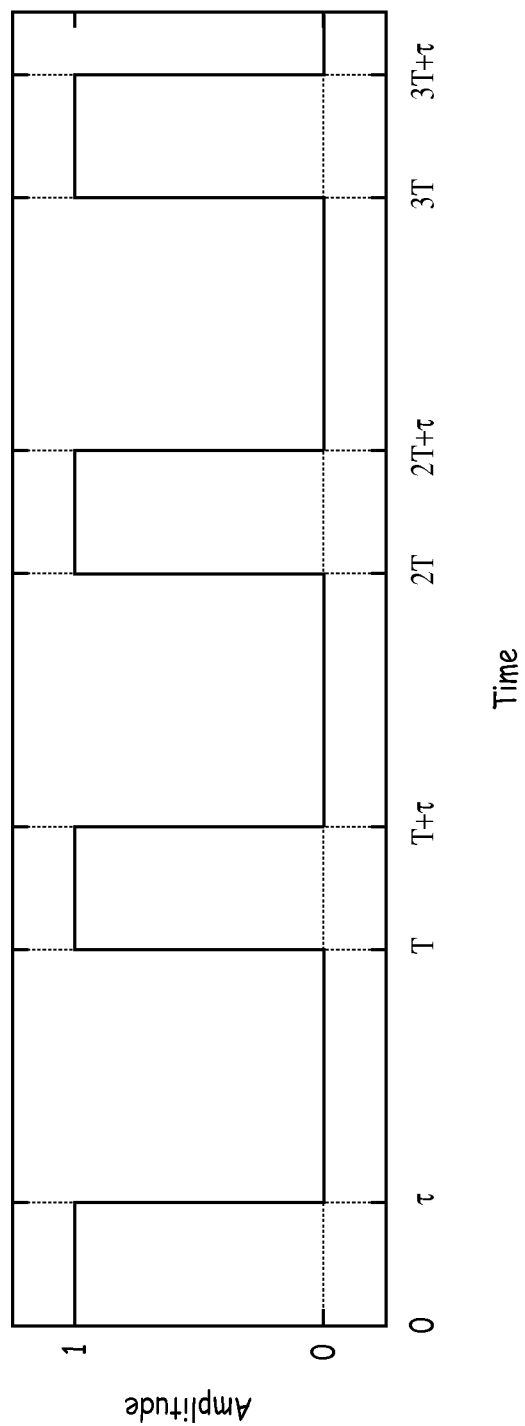
FIG. 9A is an illustration of an exemplary duty cycle of a power source.

Power sources such as RF generators may produce power according to a duty cycle, an example of which is shown in FIG. 9A. A duty cycle is periodic, and may be calculated as the fraction of time that a system (such as a power source) is in an active state, as opposed to an inactive state. For example, the duty cycle may equal a time that the power source is active divided by the period of the function or operation of the power source. The duty cycle may vary or be adjusted many times during the course of a single procedure, based on temperature and impedance feedback from the site or local area of the ablation element or array. Other means of controlling the power output are possible as well, including varying the voltage output of the RF generator.

Sensors on the medical device may provide feedback to the system which can be used to control the power source and provide a safe and effective ablation. In other words, the ablation system may continuously monitor the power source and the local conditions near each ablation element, modulating operation of the power source accordingly. One example of a control system is a proportional-integral-derivative ("PID") controller, which is a control algorithm using a feedback loop that calculates a difference between the process variable, i.e., the current conditions, properties, or feedback, and a desired goal value or setpoint. This difference may be called a gap value or error signal. The controller then adjusts the power source operation, which may include the duty cycle, to minimize the value of the error signal or gap value between the process variable and the setpoint. The PID controller may use a software program or algorithm to evaluate three separate parameters, the proportional, integral, and derivative values. The proportional value is based on the current error signal times a proportional gain, the integral value is based on the sum of recent error signals times an integral gain, and the derivative value is based on the rate at which error signal has been changing, times a derivative gain. The controller output is the sum of the proportional, integral, and derivative values. In addition, the integral term of the controller has a parameter, called the integral period, that determines the length of time for which the past error signals are summed or integrated. An integral period of sufficient duration allows the controller to act as a low-pass filter, rejecting high-frequency signals that would otherwise cause undesirable variations in the output of the controller. If the integral and derivative gain values are both zero, the controller's output depends only on the proportional gain times the error signal. This is called proportional or P-control. If the derivative gain is zero, and the proportional and integral gains are non-zero, then the controller is called a P-I controller.

In the case of a medical method in which the power source is an RF generator, and in which a medical device has an ablation electrode, a power level may be selected including the selection of a desired maximum power. The power source may deliver energy at variable levels controlled by using a duty cycle as shown in FIG. 9A. The source of energy coupled to the ablation element thus has a duty cycle of selectable duration within a base frequency. In other words, the duty cycle is the fraction of T, the time when the power source is active, divided by T, the period of the duty cycle. This variable duty cycle produces a selectable or variable power output. To avoid generation of coagulum during an ablation procedure, it may be suitable to increase the fidelity of the power control system by reducing the wavelength or base frequency. Such a lower base frequency may result in better control of the power source, and may improve heat dissipation from the ablation element. The shorter duty cycle base frequency means each instance in which an RF ablation system generates energy and associated heat has a shorter active period. Such a shorter active period allows heat to dissipate more effectively through conduction, convention, or fluid flow including a liquid such as blood flow. A corresponding increase in thermal dissipation reduces a possible opportunity for coagulum to form. In a specific example, an RF generator may generally have a duty cycle with a base period of approximately 15-20 ms, with a particular example being 17.6 ms, which may be reduced to approximately half of that amount at 7.5-10 ms, with a particular example being 8.8 ms. In other words, the period of the duty cycle may be reduced to a time of at most 10 ms, for example. Such a shorter duty cycle period results in shorter activation times, which provides more efficient heat dissipation, as well as greater fidelity in control and responsiveness during operation of the RF generator.

A medical system may include a medical device having an ablation element and a feedback sensor, a source of energy having variable power output, and a proportional-integral-derivative ("PID") controller. The energy source is operatively coupled with the ablation element and feedback sensor. The PID controller is coupled to the feedback sensor and the source of energy, and the parameters of the PID controller may be selected to reduce a possibility of coagulum.

A medical system may have a medical device with an ablation element and a feedback sensor, a source of energy having a variable power output which is in operative communication with the ablation element and feedback sensor, and a proportional-integral-derivative ("PID") controller coupled to the feedback sensor and the source of energy, the parameters of the PID controller may be selected to reduce a possibility of coagulum. A goal may be set for operation of the ablation element, which may for example be a selected temperature, and which is adjusted over time during the course of a medical treatment. The feedback sensor provides information as to current or instantaneous conditions at or near the ablation element. If there is a difference between the goal or desired conditions and the actual conditions observed by the feedback sensor, the controller attempts to minimize this difference. Accordingly, the proportional, integral, and derivative parameters may be independently adjusted or tuned for performance, accuracy, and responsiveness. For example, given a current difference between desired and actual conditions, and a series of difference observations over time, the proportional parameter may correspond to the present or instantaneous difference, the integral parameter may correspond to an aggregate of past differences observed over time, and the derivative parameter may correspond to a prediction of future differences based on a current rate of change in the difference between desired and observed values. A weighted combination of these three parameters may be used to adjust the power source, during the course of an ablation medical treatment.

In a particular example of an ablation system for treatment of cardiac tissues, the integral parameter of a PID controller may be selected to have a longer period, for example at least equal to the duration of a heartbeat. Such a longer period for the integration parameter of a PID controller may slow down the response of controller to momentary oscillations, and may reduce or avoid tracking or chasing of the power source to fluctuations in feedback observations of local conditions. Accordingly, local conditions at an interface between the ablation element and the tissue to be treated may experience fewer sudden changes, and of lesser magnitude. In the case of a temperature sensor, a longer integral period may avoid temperature oscillations caused by motion, such as the movement of cardiac tissue during a heartbeat.

In an exemplary use of a medical system as illustrated in the flow diagram of FIG. 9, the medical system is first prepared for ablation, and the ablation system is set up. One or more ablation elements are placed in contact with tissue to be treated. Various ablation parameters are determined, which may include for example the intended duration of ablation, desired power, and/or desired temperature. A power level of energy to ablate tissue is selected, and energy is delivered at the selected power level to the ablation element. The medical system continuously monitors feedback information from the ablation element and evaluates whether the ablation element is in continuous contact with the tissue, using one or more of the techniques described below. If the ablation element is not in continuous contact with the tissue, the power level is prevented from increasing (e.g., either decreased or maintained). If the ablation is complete, the medical system stops delivering energy.

During a particular medical method, a power source may be coupled to a medical device having at least one ablation element such as for example an electrode. The ablation element of the medical device may be advanced into contact with tissue to be treated. The physician may then observe various parameters, including for example a cardiac pulse waveform, individual or aggregate electrical signals from the ablation elements, confirming positioning of the distal treatment assembly, and setting various parameters on the power source. A power level of energy may be selected to ablate the tissue. Upon activation by the physician, the power source begins delivering energy at the selected power level to the ablation element or elements. During activation, the electronic circuitry and/or processor of the power source monitors the feedback information provided by the medical device, which may include temperature information. Based on the feedback information, the system may determine whether an ablation element is in continuous contact, or has lost contact, or is in intermittent contact with the tissue. That is, the power delivery as set by the duty cycle is limited by algorithm when the power delivery is associated with a targeted temperature. When an ablation element ceases to be in continuous contact with the tissue, the system may respond appropriately, which may include reducing or maintaining the power level of the power source.

One possible indicator of lost or intermittent contact is that the temperature of an ablation element may drop, as compared to an average of recent temperatures. In other words, when the current or instantaneous temperature diverges from the average temperature, it may indicate the ablation element is no longer in continuous contact with the tissue. A medical method may include advancing an electrode of a medical device into contact with tissue to be treated, monitoring a temperature of the electrode by measuring instantaneous temperature, and calculating an average temperature of the electrode. A desired temperature and a threshold variation may be selected, and energy delivered to the electrode. The method may further include calculating a difference between the instantaneous temperature and the average temperature, and a delta value may be calculated by subtracting the difference from the desired temperature. Reducing the selected power level may be performed by reducing the desired temperature. The desired temperature may be reduced when the continuity value exceeds the threshold variation. In addition, a medical method may also include selecting an increment (e.g., a pre-determined temperature or power amount or factor) by which the power may be reduced. A reduction value may be calculated by multiplying the continuity value and the increment. Then the desired temperature may be reduced specifically by subtracting the reduction value from the desired temperature.

After an indication that the ablation element is not in continuous contact with the tissue, and a corresponding reduction of power level of energy from the power source, the medical system may continue to gather feedback information and evaluate whether the ablation element has regained continuous contact with the tissue. Upon determining that the ablation element has regained continuous contact, the medical device may respond appropriately, including increasing the selected power level of the power source. Accordingly, when the continuity value falls below the threshold variation, indicating the ablation element is again in continuous contact with the tissue, the desired temperature may thereafter be increased.

A particular example is illustrated in FIG. 10, relating to RF ablation of cardiac tissue. A threshold variation may be selected which is small enough to provide a rapid response to non-continuous contact, yet avoid unnecessarily frequent adjustments. An increment may be selected which is small enough to provide responsive control of the ablation process, yet which is large enough to adjust the power level if the ablation element has lost continuous contact. Any suitable threshold variation and increment may be selected. In the particular example of FIG. 10, the threshold variation has been selected as approximately 5 degrees, and the increment is approximately 1 degree. An example graph is shown in FIG. 11, in which the instantaneous temperature oscillates, the average temperature rises to maintain a relatively steady temperature of approximately 50 degrees, and an initial temperature goal has been set by an operator at 60 degrees. When the instantaneous temperature exceeds the average temperature by more than the threshold variation, the system concludes the ablation element has intermittent contact and automatically lowers the target temperature. Accordingly, peaks of current temperature may be controlled to magnitudes within the threshold variation.

A decay or delay interval may also be selected, such that a subsequent increase in power level is performed only after the ablation element has continuous contact with the tissue for a time at least equal to the delay interval. In some situations if the instantaneous temperature experiences large or consistent fluctuation, it may momentarily dip below the threshold variation, yet soon or immediately rise above the threshold variation again. Using a delay interval may have the benefit of waiting a designated time period before allowing the temperature goal to reset, resulting in a more stable power control system. As a particular example, the delay interval may be selected at approximately 3 seconds.

In a medical device having a plurality of ablation elements, the processes of delivering energy to and monitoring feedback from the ablation element, determining whether the ablation element has ceased to be in continuous contact with the tissue, and reducing the power level of the power source may be performed individually with respect to each ablation element.

Figure 12:
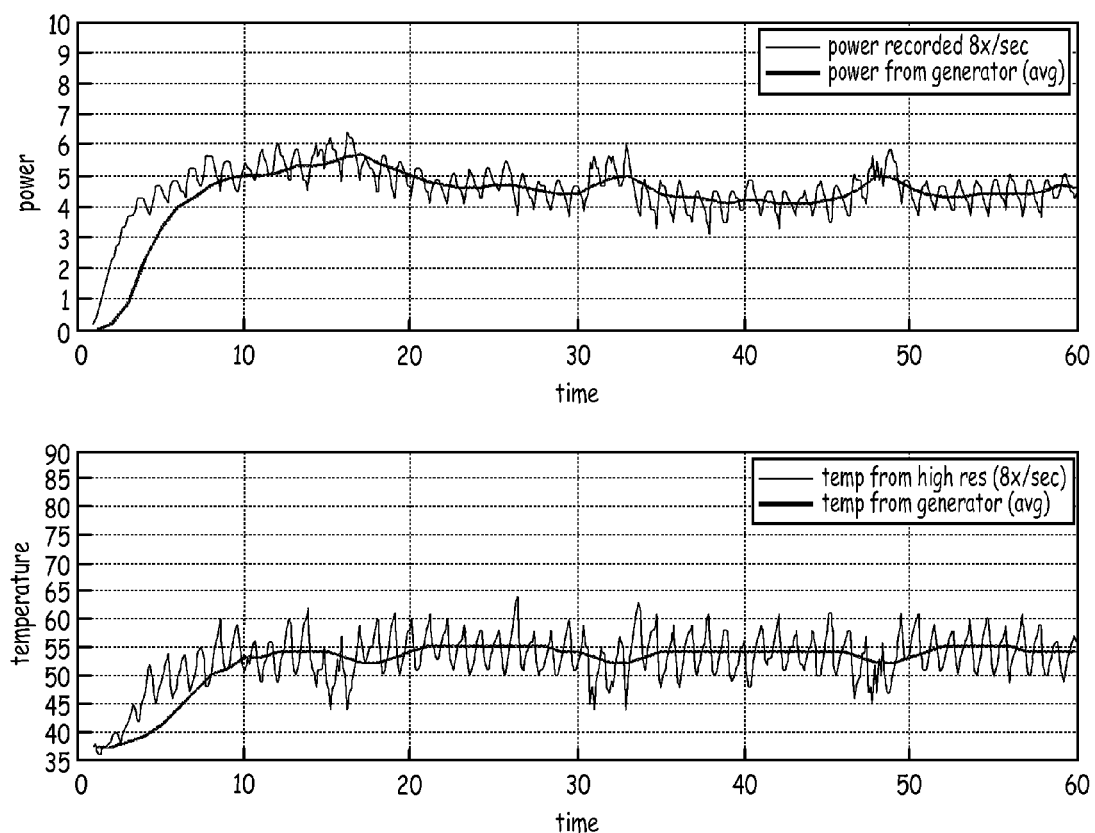
FIG. 12 is a graph illustrating exemplary parameters during the medical method of FIG. 10.
Figure 13:
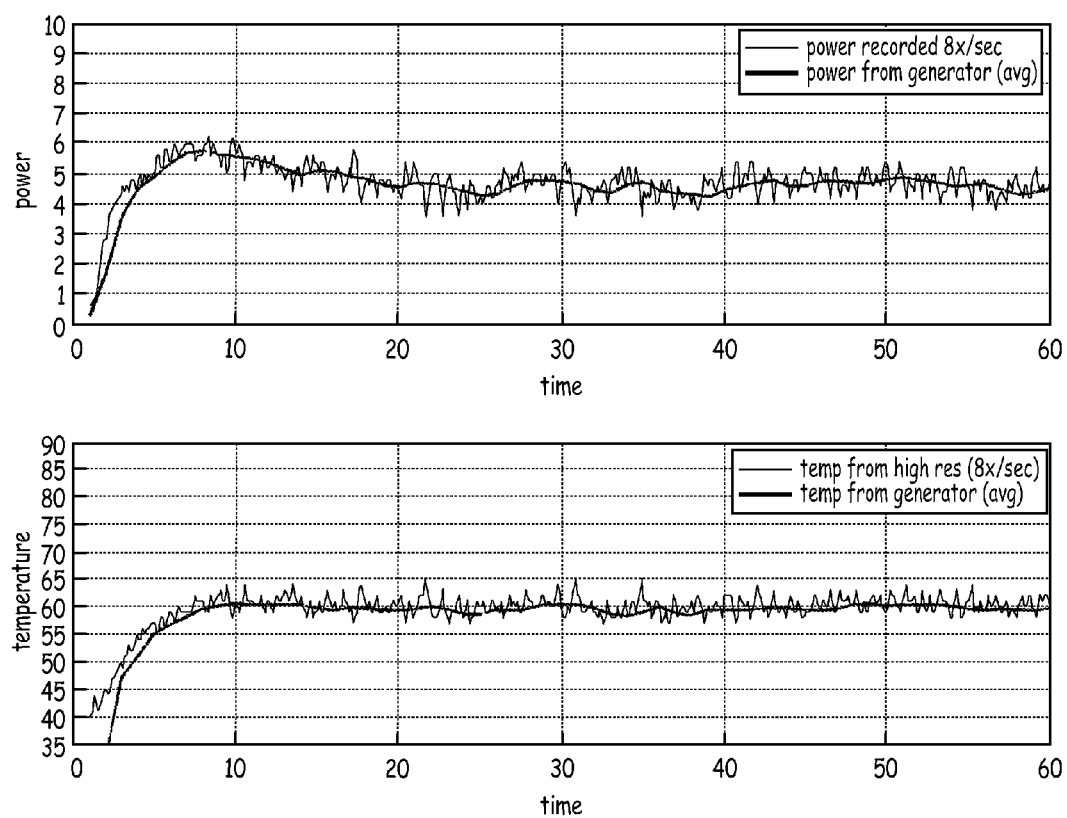
FIG. 13 is a graph illustrating exemplary parameters during the medical method of FIG. 10.

FIGS. 12 and 13 show comparative graphs of another specific example system, in which FIG. 12 illustrates temperature feedback having relatively large and consistent oscillation, using a power control algorithm to respond accordingly. This response is indicated by the corresponding oscillating power curve, so as to maintain maximum temperatures within a threshold variation of a temperature goal. In this particular example, the threshold variation has been selected at 5 degrees, and the temperature goal at 60 degrees. In a contrasting example of temperature feedback having relatively little oscillation as shown in FIG. 13, the same power control algorithm applies more subtle control to maintain the desired temperatures and optimize ablation performance.

With reference to FIGS. 14-18, a medical method may also include advancing an electrode of a medical device into contact with tissue to be treated. A desired temperature and a threshold temperature value may be selected. Energy is delivered from a power source at a duty cycle value to the electrode. Power produced by the power source may be monitored, as well as a temperature of the electrode. A duty cycle limit may be set equal to an initial duty cycle value, and energy is limited to a maximum duty cycle limit when the measured temperature exceeds the threshold temperature.

Figure 14:
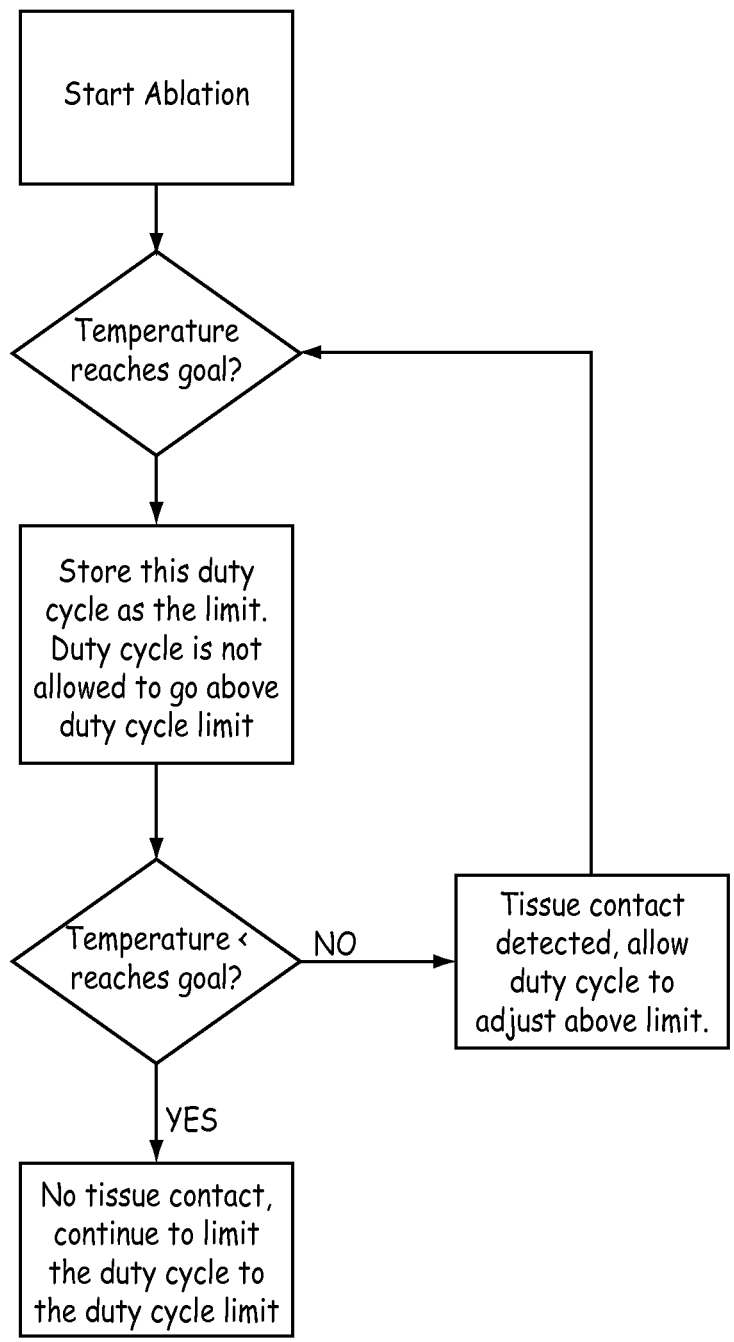
FIG. 14 is another flow chart of a medical method of use of the medical systems of FIGS. 1-8 in accordance with the principles of the present invention.
Figure 15:
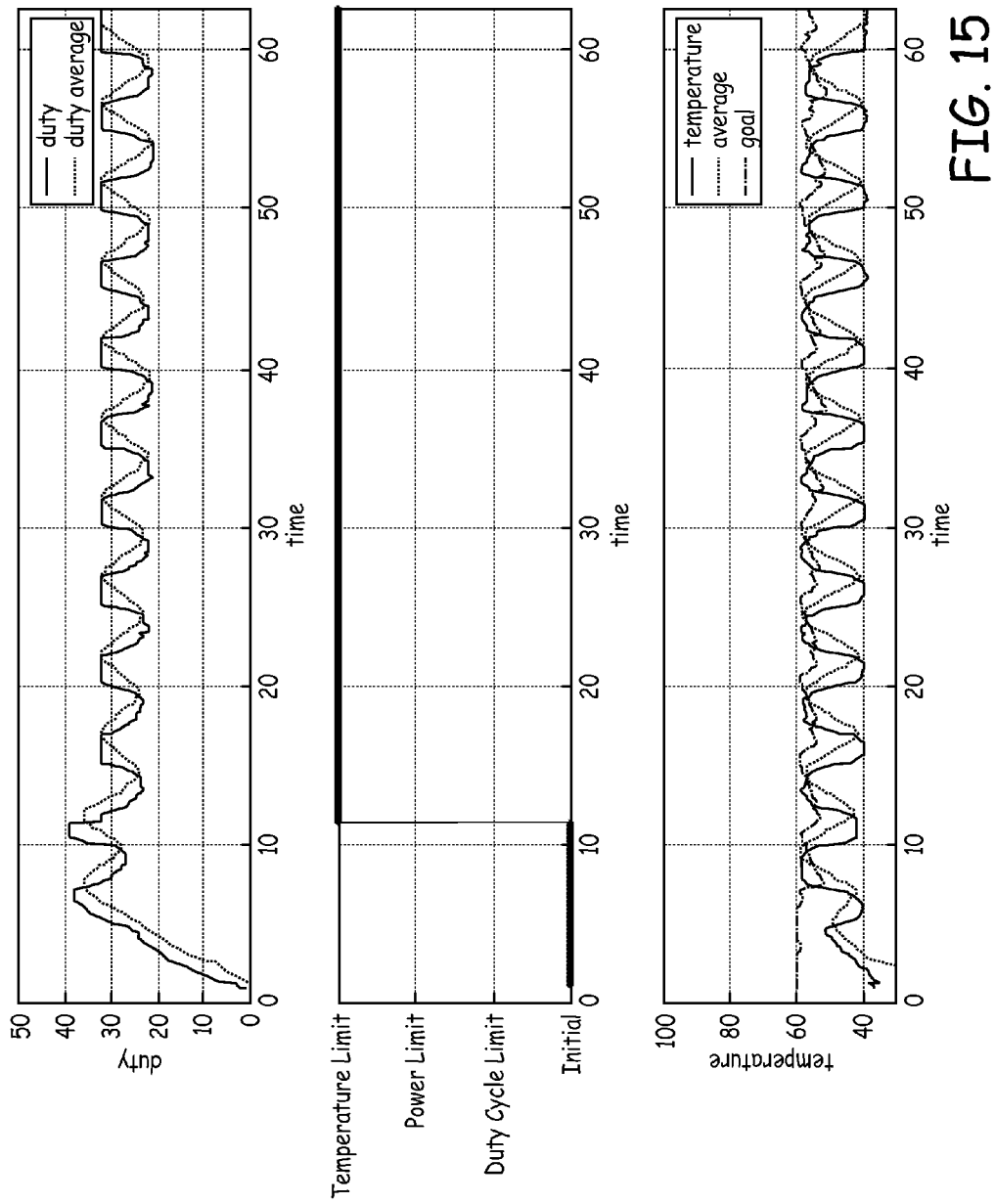
FIG. 15 is a graph illustrating exemplary parameters during the medical method of FIG. 14.

With reference to FIG. 14 and a particular example of an RF ablation generator with power output modulated by duty cycle, a sensor may be provided such as a temperature sensor which is near or touching an ablation element or an interface between the ablation element and the tissue. A desired temperature may be selected, ablation may begin, and a temperature of the ablation element may be monitored. If the temperature is not at least equal to the desired temperature, the current duty cycle may be stored in memory as a maximum limit of the duty cycle. If the temperature exceeds the temperature threshold, then it may be concluded the ablation element has contacted the tissue to be treated, and the control system may allow the duty cycle to adjust above the current duty cycle limit. However, if the temperature is below the temperature threshold, then it may be concluded the ablation element is not in contact with the tissue to be treated, and the control system may continue to limit the duty cycle to, at most, the current duty cycle limit. Operation according to this particular example is illustrated in FIG. 15, showing a duty cycle being limited in the horizontal portions of the duty cycle graph.

Figure 16:
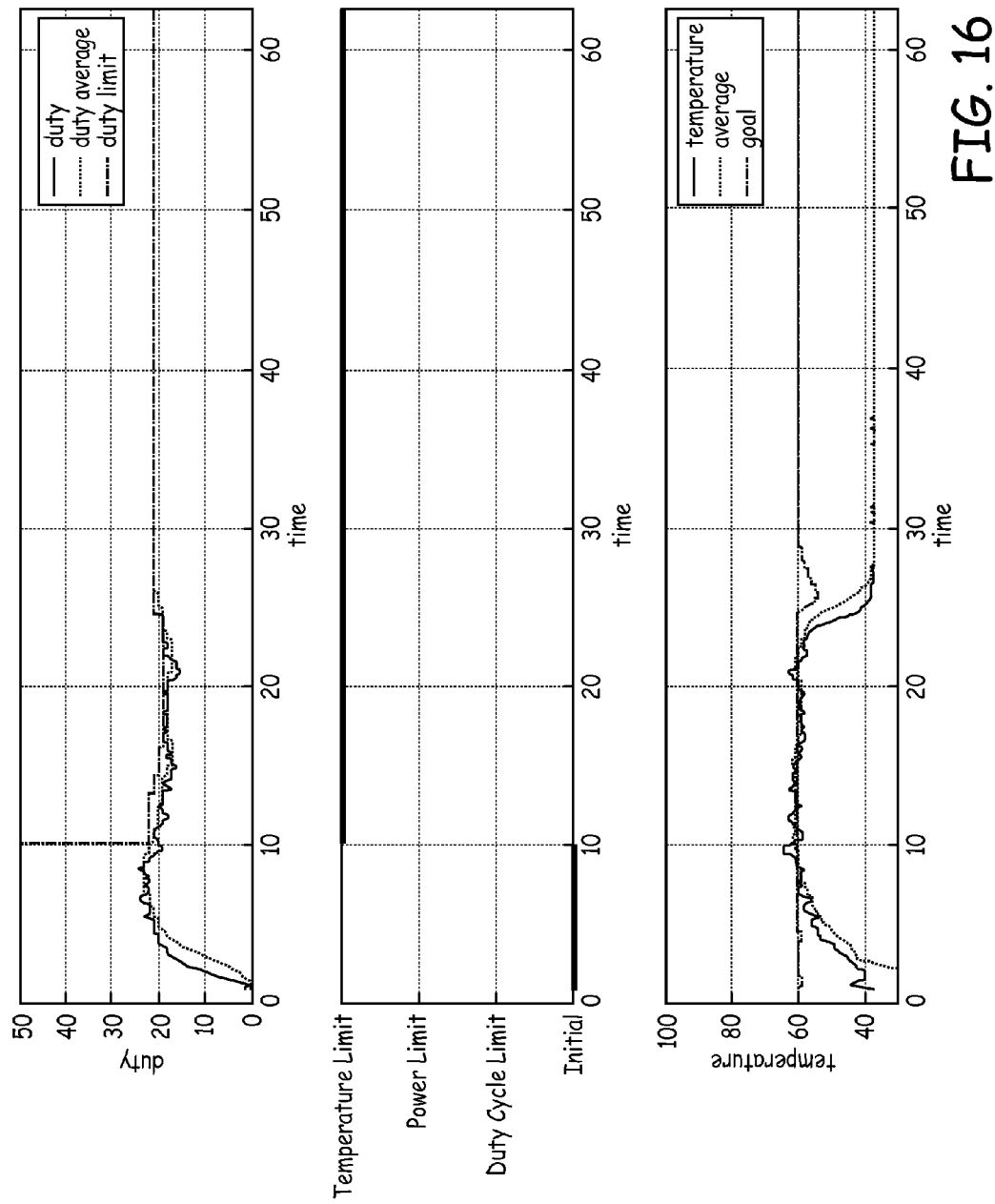
FIG. 16 is a graph illustrating exemplary parameters during the medical method of FIG. 14.
Figure 17:
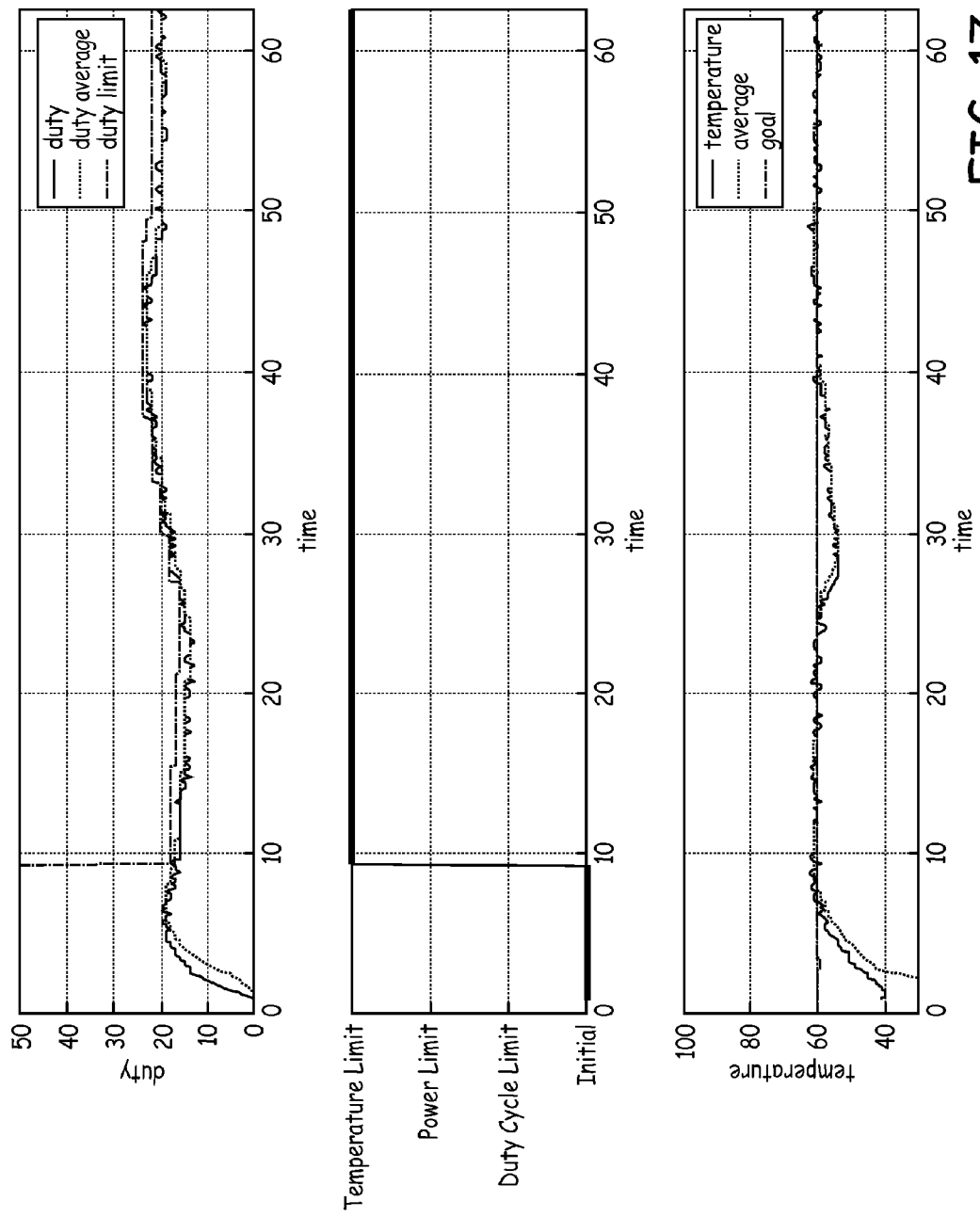
FIG. 17 is a graph illustrating exemplary parameters during the medical method of FIG. 14.
Figure 18:
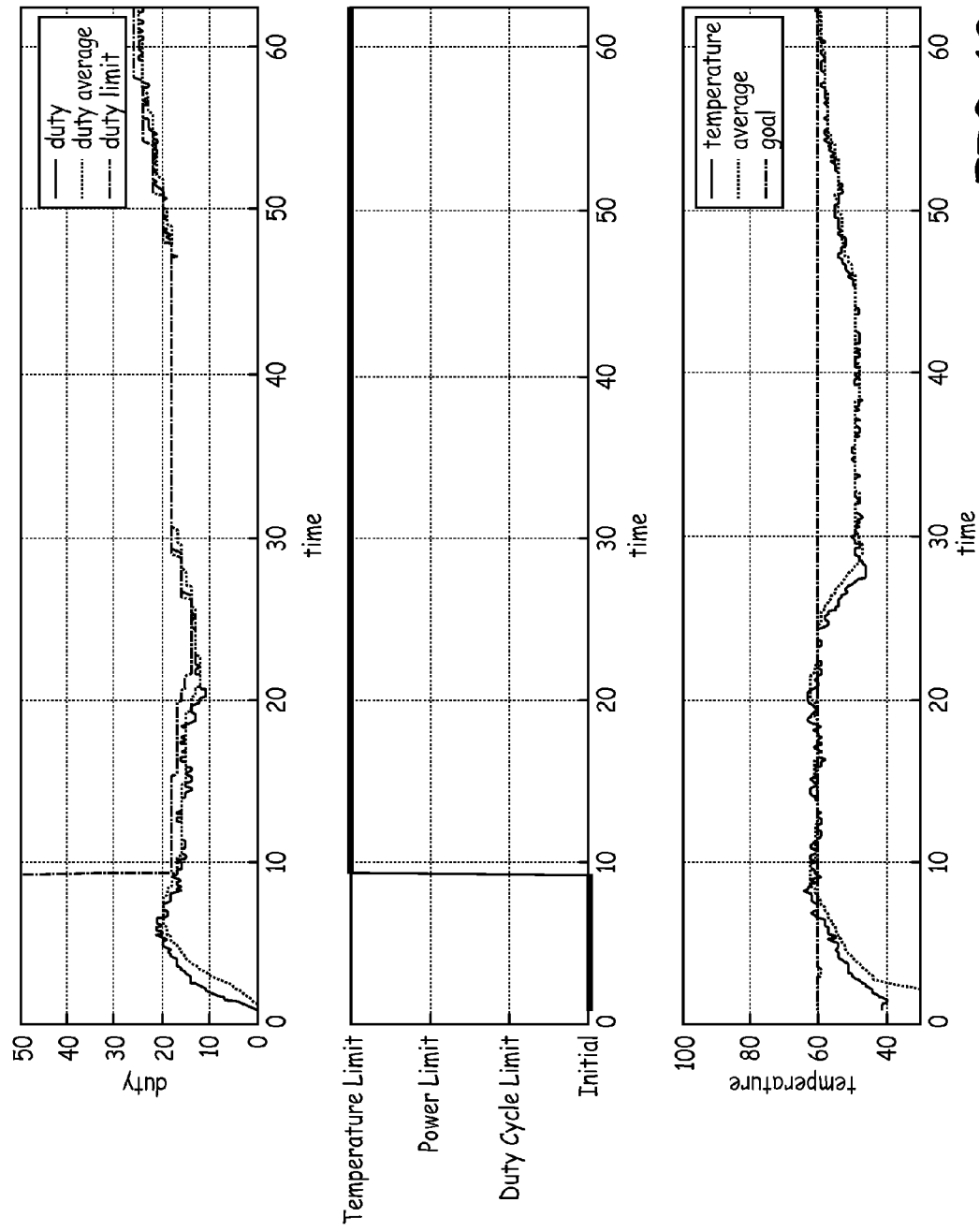
FIG. 18 is a graph illustrating exemplary parameters during the medical method of FIG. 14.

Specific examples of data recorded during operation of an example system are shown in FIGS. 16-18. In particular, FIG. 16 illustrates a scenario in which an ablation element has continuous contact with the selected tissue for approximately 20 seconds, followed by no contact with the tissue. The temperature initially ascends above a previously selected threshold temperature of 50 degrees and maintains at approximately a desired temperature of 60 degrees. Of course, the threshold temperature and desired temperature may be selected to have any suitable or preferred magnitudes. After 20 seconds, the temperature descends to below 40 degrees, and the algorithm recognizes that the electrode or ablation element has lost continuous contact with the tissue. The algorithm accordingly limits the duty cycle of the power source thereafter.

Another specific example is shown in FIG. 17, depicting a scenario in which an ablation element has continuous contact with the selected tissue for the duration, with a momentary adjustment in contact after 20 seconds. The temperature initially rises above a previously selected threshold temperature of 50 degrees and maintains at approximately the desired temperature of 60 degrees. After 20 seconds, the temperature falls slightly but remains above the previously selected threshold temperature of 50 degrees. The algorithm recognizes that the ablation element is not in continuous contact with the tissue. The algorithm accordingly allows the duty cycle to increase and optimize the ablation.

FIG. 18 shows a specific example similar to FIG. 17, in which an ablation element has continuous contact with the selected tissue for the duration, with a momentary adjustment in contact after 20 seconds. However, after 20 seconds the temperature falls below the selected threshold temperature of 50 degrees. The algorithm accordingly limits the duty cycle until the temperature again rises above the selected threshold temperature, thereafter allowing the duty cycle to increase.

Alternatively, a medical method may also be provided in which a maximum power amount is used to limit the average power, as well as the instantaneous power. An electrode may be advanced into contact with tissue to be treated, and a desired maximum power selected. Energy may be delivered from a power source at a duty cycle value to the electrode. Power produced by the power source is monitored, and average power produced by the power source is calculated. The average power is limited to the desired maximum power. When the instantaneous power reaches the desired maximum power, the corresponding duty cycle is stored as a maximum duty cycle. Thereafter, the duty cycle value is limited to the maximum duty cycle.

Of note, although the methods described herein involve target temperatures and duty cycle modifications and control logic to provide the desired treatment and power delivery characteristics, it is also contemplated that voltage control modalities may be implemented with continuous wave radiofrequency ablation devices. For example, in devices where radiofrequency power delivery is substantially constant (e.g., does not include off-periods of a duty cycle), the voltage of the delivered power or signal can be set and tailored depending on the measured and desired temperatures, akin to that described herein with respect to duty cycle modifications.

It will be appreciated by persons skilled in the art that the present invention is not limited to what has been particularly shown and described herein above. Of note, while certain components, such as the various electrodes or other items disclosed herein, are indicated as mapping, reference, and/or recording electrodes, it is understood these are exemplary functions that do not limit additional uses of the designated electrodes or components for alternative functions. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical method, comprising:
   advancing an ablation element of a medical device into contact with tissue to be treated;
   supplying power from a power source to the ablation element to ablate the tissue;
   monitoring a temperature of the ablation element;
   then determining a state of contact between the ablation element and the tissue based on the temperature of the ablation element;
   then, after a determination that the state of contact is that continuous tissue contact has been lost, initiating a reduction in the power supplied by the power source; and
   when the ablation element regains continuous tissue contact; and
   the state of regained continuous tissue contact has continued for at least three seconds, then initiating an increase in the power supplied by the power source.

2. The medical method of claim 1, wherein the tissue to be treated is cardiac tissue.

3. The medical method of claim 1, further comprising:
   selecting a desired temperature of the ablation element; and
   reducing the power to the ablation element when the monitored temperature exceeds the desired temperature.

4. The medical method of claim 1, further comprising:
   selecting a maximum limit for the supplied power to the ablation element;
   measuring the supplied power to the ablation element;
   calculating the average power supplied to the ablation element; and
   limiting the average power to the maximum threshold.

5. The medical method of claim 4, further comprising setting a maximum duty cycle equal to the current duty cycle value when the supplied power is at least equal to the maximum limit, and thereafter limiting the duty cycle value to the maximum duty cycle.

6. A medical method, comprising:
   advancing an electrode of a medical device into contact with tissue to be treated;
   delivering energy from an energy source to the electrode;
   monitoring an instantaneous temperature of the electrode;
   selecting a desired temperature and a threshold variation;
   calculating an average temperature of the electrode during the energy delivery to the electrode;
   calculating a difference between the instantaneous electrode temperature and the average electrode temperature;
   calculating a continuity value by subtracting the difference from the desired temperature;
   determining a state of contact between the electrode and the tissue and assigning a contact status, the contact status based on the continuity value and the threshold variation, a contact status of continuous contact being assigned when the continuity value is less than the threshold variation and a contact status of one of intermittent contact and no contact being assigned when the continuity value is greater than the threshold variation;
   initiating a reduction in the energy delivered by the energy source when the contact status is one of intermittent contact and no contact;

then re-evaluating contact between the electrode and the tissue and re-assigning the contact status;

determining whether the contact status is continuous contact; and when the contact status is continuous contact and has been continuous contact for at least three seconds, then initiating an increase in the energy delivered by the energy source.

7. The medical method of claim 6, wherein the threshold variation is substantially equal to 5 degrees.

8. The medical method of claim 6, further comprising selecting an increment, and calculating a reduction value by multiplying the continuity value by the increment, wherein reducing the desired temperature is performed by subtracting the reduction value from the desired temperature.

9. The medical method of claim 8, wherein the increment is substantially equal to 1 degree.

10. The medical method of claim 7, wherein the medical device has a plurality of electrodes, and wherein monitoring, delivering, calculating, and reducing are performed individually with respect to each electrode.

11. A medical method, comprising:

advancing an electrode of a medical device into contact with tissue to be treated;

monitoring a temperature of the electrode;

selecting a desired temperature and a threshold value;

delivering energy from an energy source at a duty cycle value to the electrode;

setting a duty cycle limit equal to an initial duty cycle value;

limiting the energy to a maximum of the duty cycle limit when the threshold value exceeds the temperature; and after the temperature has exceeded the threshold value continuously for at least three seconds, then increasing the duty cycle limit.

12. The medical method of claim 11, wherein the threshold value is substantially equal to 50 degrees.

* * * * *